United States Patent [19]

Eckstein et al.

[11] 4,146,597

[45] Mar. 27, 1979

[54] RESPIRATORY AIR HUMIDIFIER FOR RESPIRATORS

[75] Inventors: Wolfgang Eckstein, Sereetz; Frank Benthin, Lubeck-Israelsdorf, both of Fed. Rep. of Germany

[73] Assignee: Dragerwerk Aktiengesellschaft, Fed. Rep. of Germany

[21] Appl. No.: 789,681

[22] Filed: Apr. 21, 1977

[30] Foreign Application Priority Data

Apr. 24, 1976 [DE] Fed. Rep. of Germany ....... 2617985

[51] Int. Cl.² .................... B01F 3/04; A61M 15/00
[52] U.S. Cl. .................... 261/104; 128/186; 261/107; 261/DIG. 65
[58] Field of Search .............. 261/104, 107, DIG. 11, 261/DIG. 65, 99; 55/16; 210/321 R, 321 A, 321 B; 128/186–188, 192–194, 212

[56] References Cited

U.S. PATENT DOCUMENTS

| | | | |
|---|---|---|---|
| 3,228,877 | 1/1966 | Mahon | 210/321 B X |
| 3,342,729 | 9/1967 | Strand | 55/16 X |
| 3,403,531 | 10/1968 | Oesterheld | 261/DIG. 11 |
| 3,735,558 | 5/1973 | Skarstrõm et al. | 55/16 |
| 3,856,475 | 12/1974 | Marx | 55/16 X |
| 3,871,373 | 3/1975 | Jackson | 261/104 X |
| 3,912,795 | 10/1975 | Jackson | 261/104 X |
| 3,953,334 | 4/1976 | Brun et al. | 210/321 R |
| 4,010,748 | 3/1977 | Dobritz | 261/DIG. 65 |

*Primary Examiner*—Richard L. Chiesa
*Attorney, Agent, or Firm*—McGlew and Tuttle

[57] ABSTRACT

A respiratory air humidifier comprises a plurality of hollow tubules having walls of a foil material which is impermeable to water but is permeable to steam vapor. The tubules have inside diameters of less than 300 microns and are about 15 microns thick. Breathing gas to be humidified is directed over one side of the foil for example through the tubules and the water is directed over the opposite side for example the exterior of the tubules.

1 Claim, 3 Drawing Figures

RESPIRATORY AIR HUMIDIFIER FOR RESPIRATORS

BACKGROUND OF THE INVENTION

1. Field of the Invention

This invention relates in general to the construction of humidifiers and in particular to a new and useful respiratory air humidifier which includes foils of a material which is impermeable to water but permeable to steam or vapor formed as individual walls or a plurality of hollow tubules.

2. Reference to Copending Application

This invention is an improvement over an invention disclosed and described in U.S. Pat. No. 4,010,748.

This patent discloses a respiratory air humidifier which contains a water impermeable but vapor or steam permeable foil which is charged on one side while the gas to be humidified passes over the other side. The construction describes in detail an evaporation surface of star-shaped form which achieves a large evaporation output. The present invention is an improvement over such a construction inasmuch as it provides means for further reducing the size of the respiratory air humidifier without reducing the evaporation surface and thus the evaporation output.

3. Description of the Prior Art

The invention concerns respiratory air humidifiers for respirators with surface evaporation where the evaporation surface is formed by a water-impermeable, but vapor-permeable foil which is charged on one side with water, and where the gas to be humidified passes over the other side charged with gas.

Comfort in a technical sense is the condition of well being with regard to the climate of a room to a person using this room. It depends on the temperature, the velocity of the air, and not insubstantially on the vapor pressure. The relative humidity should not be too high, or humid, but not too low, or dry, either. If too dry the air passages will dry out.

Subdivided according to the principal design, the following respiratory air humidifiers are known:

Cascade humidifiers have a system in which the inhaling air is conducted through the heated water to humidify the air. Water droplets, which have been carried along, are retained over granules arranged above the water surface. A disadvantage of the cascade humidifiers is that the compressible volume varies with the amount of water fill. Beyond that, the apparatus is so large that it cannot be arranged in front of the patient's mouth for respiration. With long feed lines, the air cools off, however. This way a part of the moisture contained in the inhaling air is condensed. The condensate must be kept away from the patient by extra devices. (Cascade Humidifiers by Bennet, Santa Monica, California, 1971).

Wick-type humidifiers operate like the cascade humidifiers, also as surface humidifiers. But due to the wick, the air does not come in such close contact with the water. It passes over the moistened wicks, which absorb heated water from a storage vessel. These humidifiers have the same disadvantages as the cascade humidifiers. But since they can be made smaller, they can be arranged close to the patient. The problems of condensation are thus more favorable, but on the other hand, sufficient humidification of the respiratory air is not always secured.

Another humidifier uses hot steam injection into the inhaling air current. For generating the hot steam, a heated plate is arranged in the humidifier on which an adjustable amount of water is evaporated. The resulting steam arrives in the inhaling air system and humidifies the inhaling air. Humidifiers working on this principle can be made very small. Condensation is therefore not a problem. Difficult, however, is the adjustment of the proper amount of water for humidifying the respiratory air. With low breathing volumes, this may result in overheating, with a too large breathing volume, on the other hand, the air may not be sufficiently humidified and the temperature may be too low.

According to the invention the foil forms a wall of hollow fibers with an inside diameter of 300 microns, and is about 15 microns thick.

The decisive advantage of this construction lies substantially in the much larger evaporation surface, which can be accommodated with the same cross-section and the same length. The aspect ratio compared to the known star-shaped arrangement is 50:1. The respiratory air humidifier according to the invention can thus be made much smaller with the same evaporation output.

In one embodiment of the invention, the gas-carrying hollow fibers arranged parallel to each other in a housing as an assembly, as well as a perforated water feed pipe and a water discharge pipe, both arranged inside the assembly, are secured on the end faces in a sealing compound.

The water required for the evaporation is fed safely on the shortest way. By wetting the surfaces from hollow to hollow fiber, the necessary uniform admission with water is ensured. The desired humidification of the gas (in the present case the respiratory air) conducted through the interior of the hollow fibers is also correspondingly safe. The easily dosable amount of water or the regulation of the amount of respiratory air flowing through the device ensures any desired humidity value in the respiratory air. The water which has not entered the hollow fibers is discharged in a simple manner through the water discharge pipe.

The design of the water feed pipe and of the water discharge pipe as a U-shaped pipe with the connections arranged side by side in the direction of the hollow fibers and secured in the sealing compound makes the technical production simple. In this embodiment only the connection to a water supply is required.

In a further development of the invention, which is of advantage for large amounts of respiratory air, the water-carrying hollow fibers are arranged on a plate, side by side in two layers arranged in a right angle to each other on both sides and secured over an air passage in a sealing compound. The water supply and discharge are effected by connecting spouts to an end bore in the sealing compound.

In addition to the advantage of a larger amount of respiratory air with a lower resistance to flow, this embodiment permits further simplification of the production. The hollow fibers are wound about the plate provided with the air passage crossed over in two layers. In this position they are cast on the four sides of the plate with the sealing compound which can be a filler. The hollow fibers are cut up through bores extending from opposite diagonal points toward both sides into the filler and are provided with free connections for the water supply and its discharge.

Accordingly it is an object of the invention to provide a respiratory air humidifier which comprises foil means of a material which is impermeable to water but permeable to steam and which includes means for directing water over one side of the foil means and means for directing breathing gas to be humidified over the other side of the foil means wherein the foil means comprises individual walls of a plurality of hollow tubules having inside diameters of less than about 300 microns and being of about 15 microns thick.

A further object of the invention is to provide a respiratory air humidifier which includes a conduit having an connection piece at one end with small size passages which communicate with the interiors of individual tubes made of material which is permeable to vapor and impermeable to water and which further includes centrally arranged enlarged water carrying conduit or pipe having a plurality of perforations or openings therein for the distribution of water over the individual tubules and a discharge pipe for carrying away the water which is circulated over the oustide surface of the tubules.

A further object of the invention is to provide a humidifier which is adapted to be disposed in a respiratory airstream which includes a plate having individual tubules stretched across the plate and longitudinal and transverse directions and which communicate through end bores or passages with water and which define a grid through which the air to be humidified is circulated.

A further object of the invention is to provide a humidifier which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there are illustrated preferred embodiments of the invention.

GENERAL DESCRIPTION OF THE PREFERRED EMBODIMENTS

Figure 1:
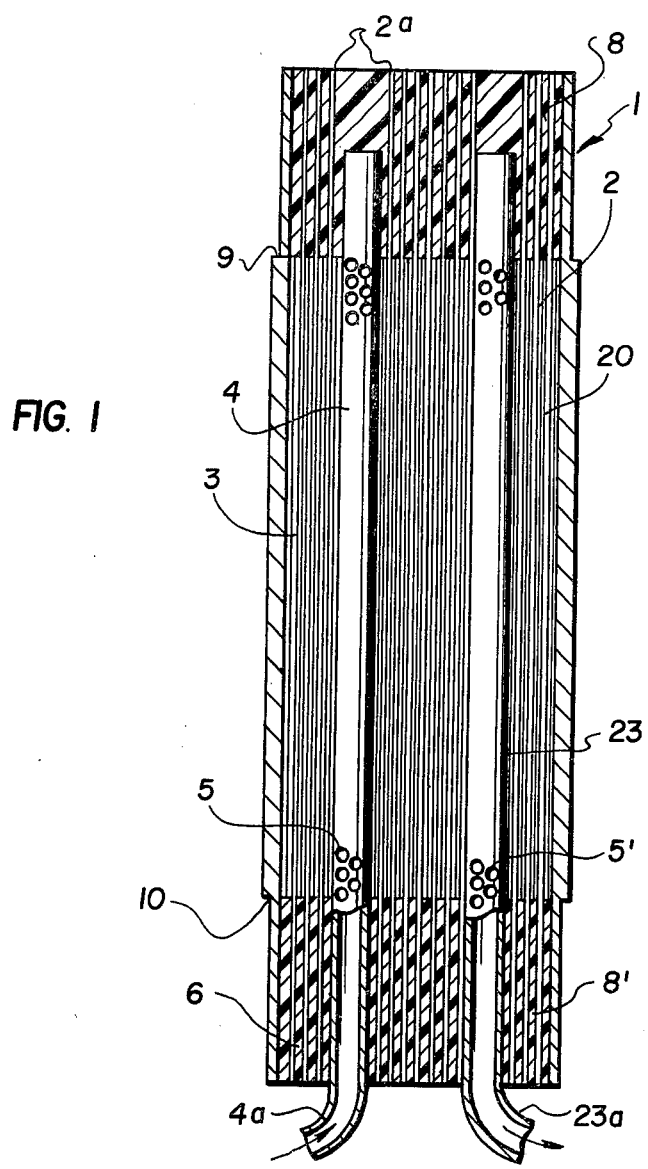
FIG. 1 is a transverse sectional view of a respiratory air humidifier having gas carrying tubules constructed in accordance with the invention.

Referring to the drawings in particular, the invention embodied therein in FIG. 1 comprises a humidifier housing generally designated 1 of tubular construction having connecting pieces or blocks 9 and 10 at respective ends which are adapted to be connected directly into a respiratory air breathing line.

In accordance with the invention the housing 1 includes an intermediate section which comprises an assembly of hollow tubes or tubules having walls which are impermeable to water but permeable to vapor or steam. Each individual tube is connected through a breathing gas connecting conduit formed in a block of sealing compound at one end and a further sealing compound 8' at the opposite or gas discharge end. Arranged within the assembly 2 and also in the end blocks 8 and 8' are water supply conduits 4 and water discharge conduit 23. With the inlet conduit 4 and the discharge conduit 23 have a plurality of perforations or holes 5 therein in the portions of these conduits which appear in a central section 20 which is located between end blocks 8 and 8' this water circulates over the exterior of the assembly of the hollow tubes 2 and flows into the holes 5' of the discharge conduit 23 and the water is then circulated out of the system. Each hollow tube or fiber member 3 is made with an inside diameter of less than 300 microns and is about 15 microns thick.

The respiratory air humidifier device housing 1 is inserted directly into a respiratory air supply (not shown). The respiratory air to be humidified then passes through all of the hollow fiber tubes 3 which are wetted on their outside with the water fed through the water feed pipe 4. Due to the vapor or steam permeable properties of the hollow fiber material the water is conducted in the form of steam to the inside of the hollow fibers and humidifiers the respiratory air which passes through these tubes. The amount of heat required for the evaporation can be supplied to the respiratory air in a known manner before it enters the respiratory air humidifier.

In the construction shown water pipe 4 has an exterior connection 4a to the exterior of the device and discharge pipe 23 has a discharge connection 23a to the exterior of the device. In some instances it is desirable to join the supply conduit 4 and the discharge conduit 23 for example by a U-shaped connection. The holes 5 and 5' are dimensioned so as to insure a controlled amount of water flow in the section 20 as desired.

Figure 2:
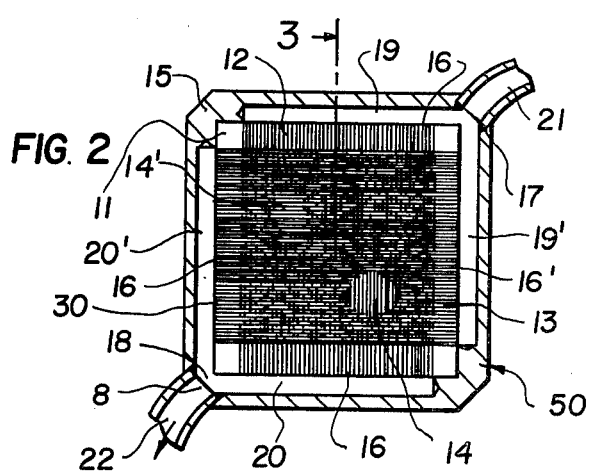
FIG. 2 is a transverse sectional view of another embodiment of the humidifier in which the water is directed into the tubules.
Figure 3:
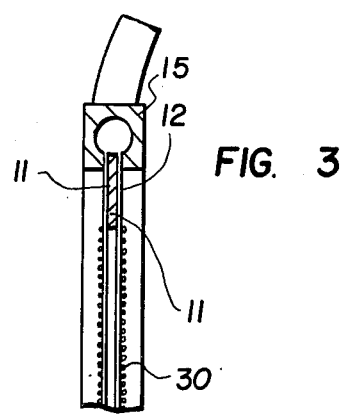
FIG. 3 is an enlarged detail portion taken along the line 3—3 of FIG. 2.

In the embodiment of FIG. 2 a humidifier generally designated 50 includes base plate 11 having grids of horizontally extending tubes 30, and vertically extending tubes arranged thereover in a pattern. A plurality of vertical tubes 30 forms a layer 12 and a plurality of the horizontal tubes 30 forms a layer 13. The tubes 12 and 30 are arranged at right angles to each other and the individual tubes of each layer are located side by side. Plate 11 over which they are wound has one or more air passages 14, 14' through which the respiratory air is directed so as to pass through two sets of tubes 30 and 12. The hollow fiber tubes 30 and 12 are cast tightly and firmly at four sides 16 of plate 11 by means of sealing compound 15 which is a filler. The construction is such that end bores 19, 19' and 20, 20' are formed along each of the respective sides of the plate 16. Bores 19 and 19' communicate with a water inlet 21 so as to supply water for passage through the sets of tubes 30 through to the opposite bores 20 and 20' which communicate with a discharge spout 22. The inlet 21 and the outlet 22 are arranged at diametrically opposite connecting points 17 and 18. In the respiratory air humidifier shown in FIGS. 2 and 3 water is circulated into the interiors of the tubes making up the tube sets 12 and 30 andd the air to be humidified is passed through the air passages 14, 14'.

While specific embodiments of the invention have been shown and described in detail to illustrate the application of the principles of the invention, it will be understood that the invention may be embodied otherwise without departing from such principles.

What is claimed is:

1. A humidifier for circulating humidified air to a person to breath, comprising an assembly of a plurality of small diameter, closely spaced hollow tubes defining small flow passages therethrough, support means supporting said tubes in a bundle with their respective ends disposed in proximity to each other, said tubes having a wall of a material which is impermeable to water but permeable to steam, said tubes having one side of its wall contactable with respiratory air and an opposite side contactable by water, first water conduit means for directing a water supply into contact with said one side of the walls of said tubes to form a vapor thereon which passes through the wall, second conduit means defining a discharge for collecting water which has been in contact with the tubes and for discharging it, means for circulating respiratory air in contact with said opposite side of said tube walls to pick up the water vapor for humidifying the respiratory air and for directing the humidified air to the person for breathing, said first water conduit means comprises the header connected to one of the common ends of said tubes for delivering water into the interior of said tubes, said second conduit means comprising a second header connecting to the opposite end of said tubes for carrying away the water which has been delivered therethrough, said means for circulating respiratory air comprises means for directing the air over the exterior surfaces of said tubes, and wherein there are two bundles of said tubes, one extending horizontally and the other extending vertically and intersecting to form a grid of said tubes, said means of circulating respiratory air passing the air through said grid, said first conduit means comprising first and second branch conduits connecting the respective ends of said horizontally and said vertically disposed tubes and said second conduit means comprising first and second discharge conduit portions connecting the opposite ends of said horizontal and vertically arranged tubes.

* * * * *